US009510963B2

(12) United States Patent
Coverdale et al.

(10) Patent No.: US 9,510,963 B2
(45) Date of Patent: Dec. 6, 2016

(54) ENDOGRAFT INTRODUCER AND A CAPSULE ASSEMBLY FOR AN ENDOGRAFT INTRODUCER

(71) Applicant: COOK MEDICAL TECHNOLOGIES LLC, Bloomington, IN (US)

(72) Inventors: Kelly Coverdale, Holland Park (AU); Werner D. Ducke, Eight Mile Plains (AU); Graham W. Scott, Springwood (AU); Mena Yang, Browns Plains (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/536,018

(22) Filed: Nov. 7, 2014

(65) Prior Publication Data

US 2015/0142097 A1  May 21, 2015

(30) Foreign Application Priority Data

Nov. 8, 2013 (AU) ................................ 2013257415
Jul. 25, 2014 (EP) ..................................... 14275159

(51) Int. Cl.
  *A61F 2/06* (2013.01)
  *A61F 2/95* (2013.01)
  (Continued)

(52) U.S. Cl.
  CPC ............... *A61F 2/95* (2013.01); *A61F 2/966* (2013.01); *A61F 2/07* (2013.01);
  (Continued)

(58) Field of Classification Search
  CPC ...... A61F 2/95; A61F 2/07; A61F 2002/9511; A61F 2/966; A61F 2002/8486; A61F 2002/9665
  See application file for complete search history.

(56) References Cited

U.S. PATENT DOCUMENTS 5,415,664 A * 5/1995 Pinchuk .................... A61F 2/95
                                                    604/523
5,693,083 A * 12/1997 Baker .................... A61B 17/11
                                                    606/195

(Continued)

FOREIGN PATENT DOCUMENTS

WO  2006102546 A1  9/2006
WO  2009148602 A1  12/2009

OTHER PUBLICATIONS

European Search Report, 14275159.3, Cook Medical Technologies LLC, Apr. 8, 2015.

*Primary Examiner* — Jing Ou
(74) *Attorney, Agent, or Firm* — Brinks Gilson & Lione

(57) ABSTRACT

A capsule assembly for an endograft introducer is disclosed. The assembly comprises: a capsule and a capsule plug. The capsule has a cavity for receiving an end of a stent graft and a capsule wall terminating in a distal end. The capsule plug comprises: a tip portion having a lead-in surface and an abutment surface; and a tail portion having an external surface engageable with an inside surface of the capsule wall. The capsule is slideably movable with respect to the capsule plug from a first position in which the distal end of the capsule wall surrounds an opening into the cavity to a second position in which the distal end of the capsule wall is positioned proximally with respect to the abutment surface, whereby movement of the tip portion into the capsule is resisted by abutment between the distal end of the capsule wall and the abutment surface.

13 Claims, 10 Drawing Sheets

(51) Int. Cl.
  *A61F 2/966* (2013.01)
  *A61F 2/07* (2013.01)
  *A61F 2/848* (2013.01)
(52) U.S. Cl.
  CPC ........... *A61F 2002/8486* (2013.01); *A61F 2002/9511* (2013.01); *A61F 2002/9665* (2013.01)

(56) References Cited

U.S. PATENT DOCUMENTS

| | | | | |
|---|---|---|---|---|
| 6,139,572 | A * | 10/2000 | Campbell | A61F 2/958 623/1.1 |
| 6,858,034 | B1 * | 2/2005 | Hijlkema | A61F 2/95 606/108 |
| 7,867,270 | B2 | 1/2011 | Hartley et al. | |
| 8,034,074 | B2 | 10/2011 | Garner et al. | |
| 2007/0067012 | A1 * | 3/2007 | George | A61F 2/915 623/1.12 |
| 2007/0123971 | A1 | 5/2007 | Kennedy et al. | |
| 2008/0033354 | A1 * | 2/2008 | Hartley | A61F 2/95 604/103.05 |
| 2008/0065011 | A1 * | 3/2008 | Marchand | A61F 2/2433 604/103.02 |
| 2009/0099637 | A1 | 4/2009 | Barthold et al. | |
| 2009/0192518 | A1 | 7/2009 | Golden et al. | |
| 2010/0100167 | A1 * | 4/2010 | Bortlein | A61F 2/2436 623/1.11 |
| 2010/0198328 | A1 * | 8/2010 | Hartley | A61F 2/95 623/1.11 |
| 2011/0144735 | A1 | 6/2011 | Hartley et al. | |
| 2011/0307048 | A1 | 12/2011 | Ivancev et al. | |
| 2012/0226341 | A1 | 9/2012 | Schreck et al. | |
| 2012/0239130 | A1 * | 9/2012 | Hartley | A61F 2/95 623/1.12 |
| 2013/0110041 | A1 * | 5/2013 | Farag | A61F 2/95 604/95.01 |
| 2013/0231735 | A1 * | 9/2013 | Deem | A61F 2/243 623/2.11 |

* cited by examiner

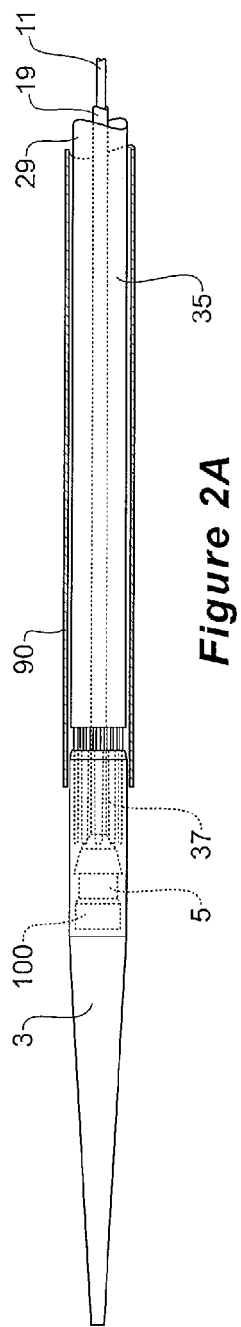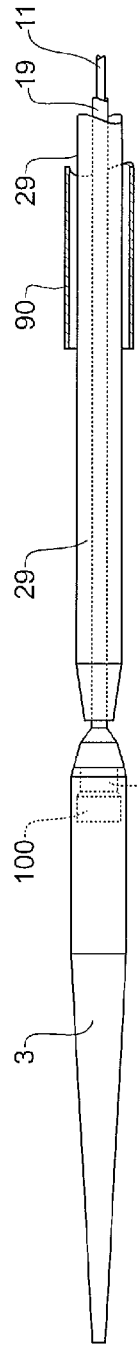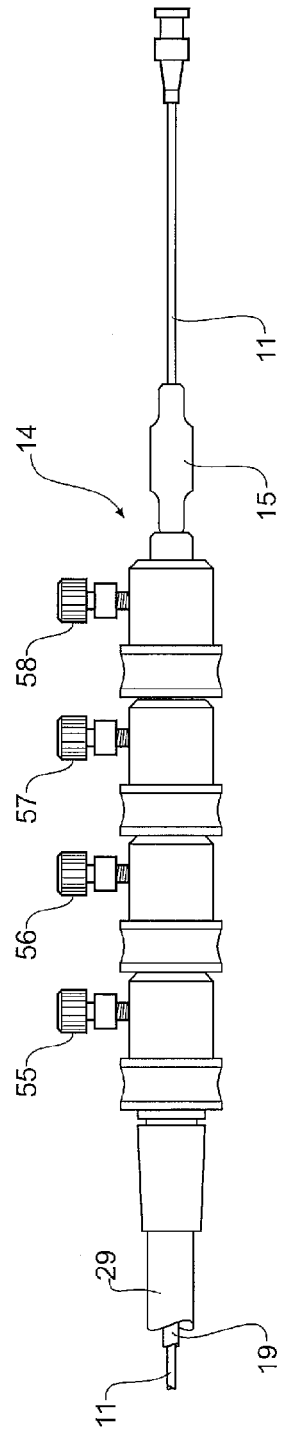
Figure 2A
Figure 2B
Figure 2C

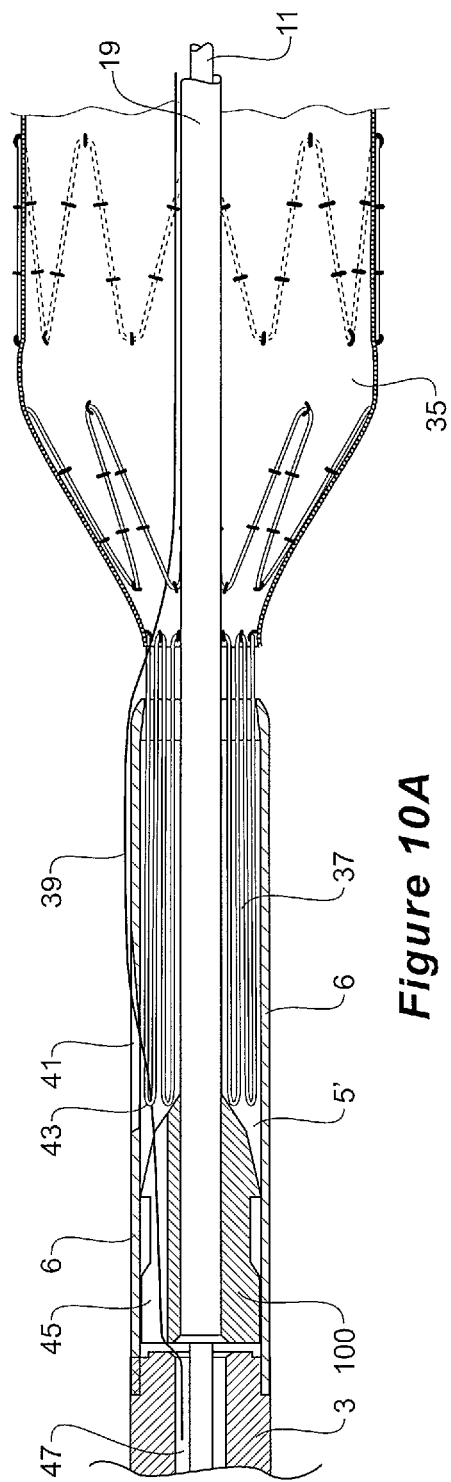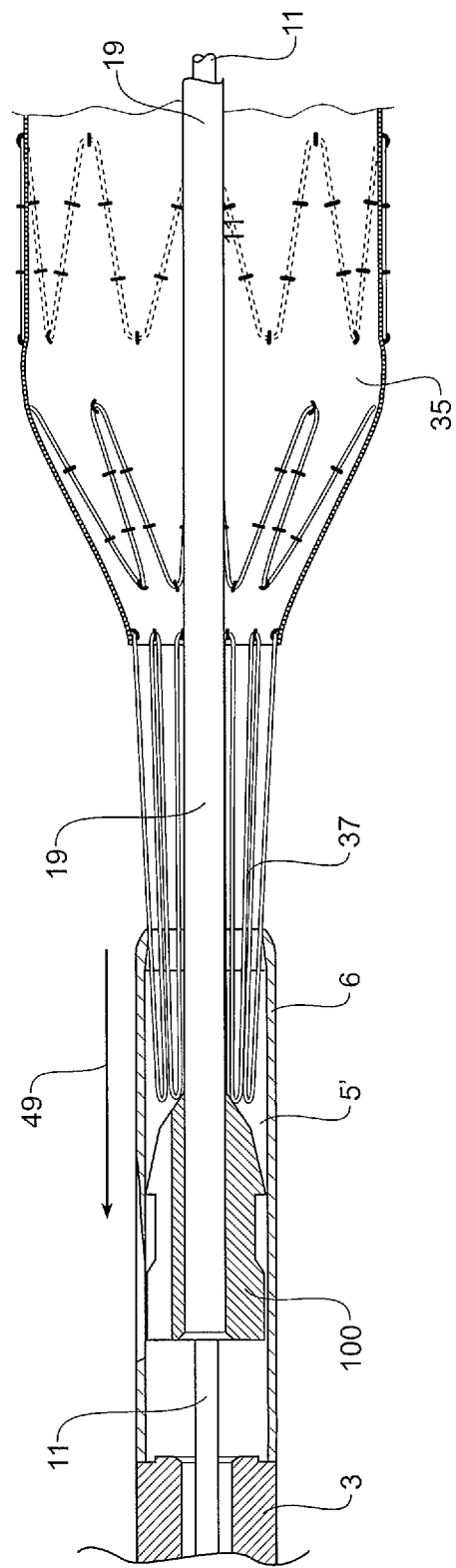

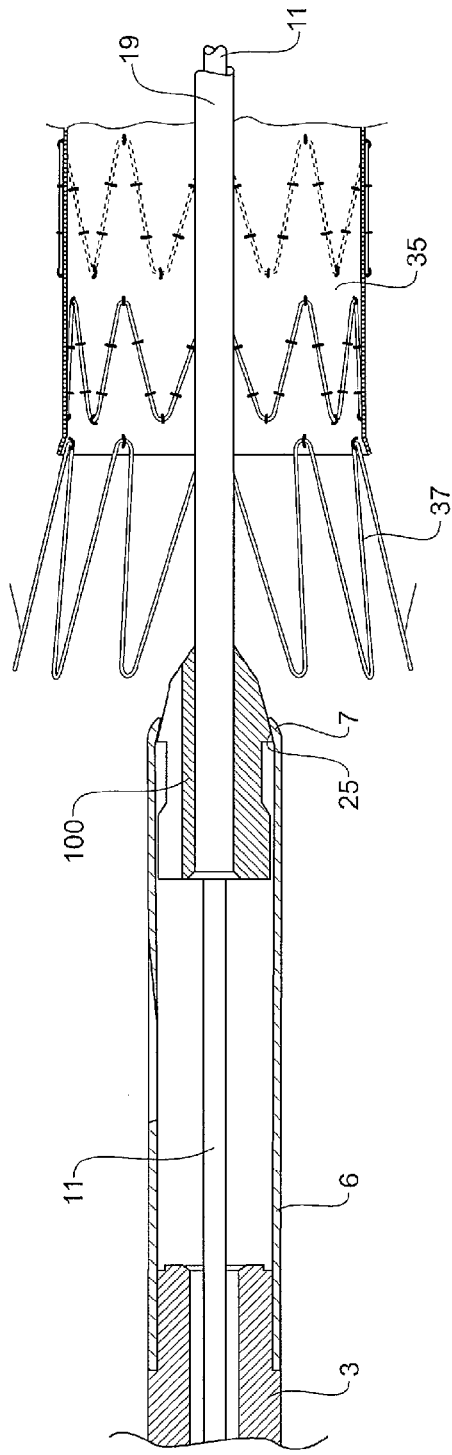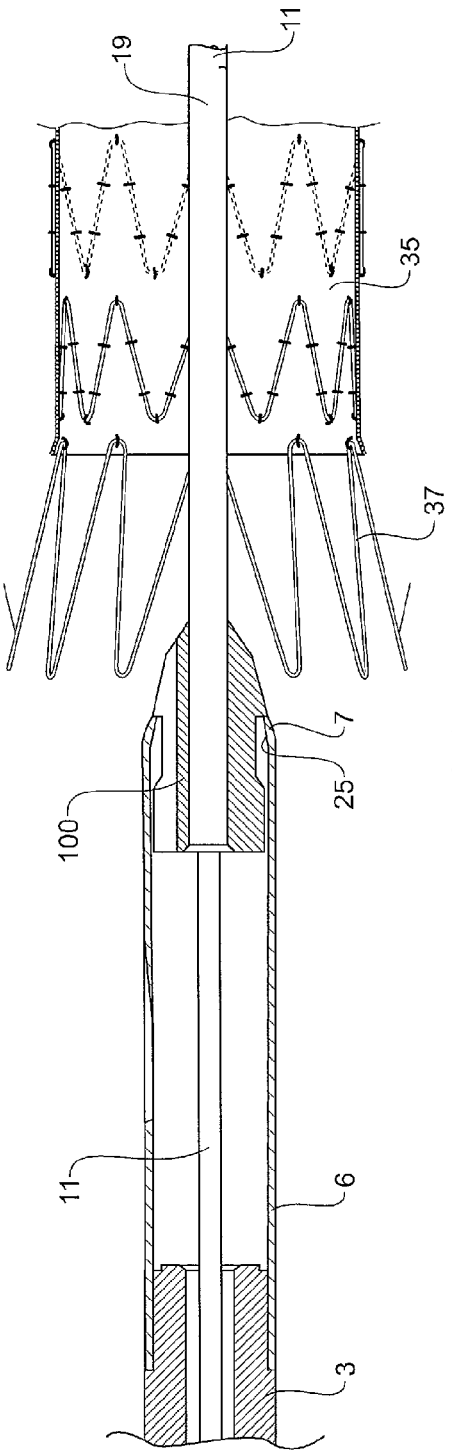
Figure 10C
Figure 10D

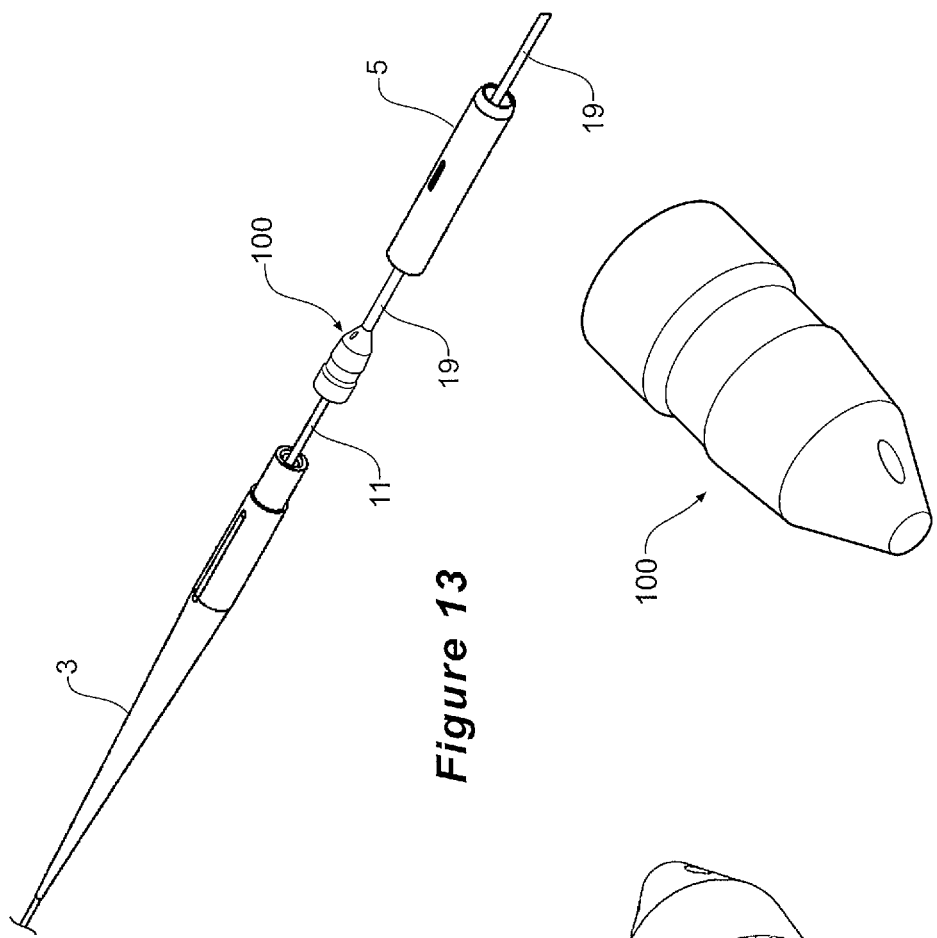
*Figure 13*
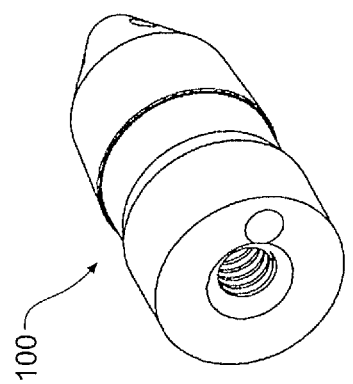
*Figure 14*
*Figure 15*

ENDOGRAFT INTRODUCER AND A CAPSULE ASSEMBLY FOR AN ENDOGRAFT INTRODUCER

TECHNICAL FIELD

The invention relates to medical devices and more particularly to a medical device used for deployment of an intraluminal graft or stent graft, otherwise referred to as an introducer or a stent graft introducer. In particular, this invention relates to a top cap retrieval arrangement.

BACKGROUND

In the deployment of a graft, or stent graft, into the human or animal body via intraluminal techniques, a deployment device is used to introduce the stent graft into a lumen of the body and, after the stent graft has been deployed and expanded within the lumen, the introducer needs to be retracted.

One form of introducer uses a proximal nose cone with a distally facing capsule to encompass an exposed stent and barbs extending from the exposed stent of a stent graft during introduction and, after the stent graft has been released and the capsule has been removed from the exposed stent, the capsule along with the introducer must be withdrawn. The capsule, however, typically has a distally facing opening with an edge surrounding it and this edge can engage with stents of the deployed stent graft and potentially cause problems by dislodging the stent graft from its position on the wall of the lumen.

It is known to provide moveable capsule plugs to facilitate retrieval of introducers. However, known capsule assemblies comprising capsules and capsule plugs, have various shortcomings.

It is important that a capsule plug remains in its correct position with respect to its capsule during both retrieval back through the inside of a deployed endograft such as the stent graft and then back through a potentially winding and pulsating aorta and through a sheath and a valve (such as a Captor™ valve).

It is the object of this invention to address one or more of the above problems or at least to provide the practitioner in the field with a useful alternative device.

Throughout this specification, the term distal with respect to a portion of the aorta, a deployment device or an endograft means the end of the aorta, deployment device or endograft further away in the direction of blood flow away from the heart and the term proximal means the portion of the aorta, deployment device or end of the endograft nearer to the heart. When applied to other vessels, similar terms such as caudal and cranial should be understood.

SUMMARY

According to a first aspect of the invention there is provided a capsule assembly for an endograft introducer, the assembly comprising:
a capsule having a cavity and a capsule wall, the capsule wall having an external surface and terminating in a distal end; and
a capsule plug, the capsule plug comprising:
a tip portion having a lead-in surface and an abutment surface; and
a tail portion having an external surface engageable with an inside surface of the capsule wall, wherein the capsule is slidably movable with respect to the capsule plug from a first position in which the distal end of the capsule wall surrounds an opening into the cavity to a second position in which the distal end of the capsule wall is positioned proximally with respect to the abutment surface, whereby movement of the tip portion into the capsule is resisted by abutment between the distal end of the capsule wall and the abutment surface.

In one embodiment, the distal end of the capsule wall tapers internally with an internally tapered portion before tapering externally with an externally tapered portion, resulting in a thickening of the capsule wall before thinning to an end.

In one embodiment, the tip portion diverges in a direction toward the tail portion reaching a maximum tip portion diameter at a location adjacent to or distal of the abutment surface.

In an alternative embodiment to that of the preceding paragraph, the tip portion comprises a first divergent portion and a second divergent portion, the first divergent portion diverging towards the second divergent portion and the first divergent portion diverging more steeply than the second divergent portion.

In one embodiment, the tip portion divergence decreases in a direction toward the intermediate portion.

In one embodiment, the distal end of the capsule wall has a terminal internal diameter that is resiliently expandable to allow the tip portion to move distally from the first position to the second position.

In one embodiment, the capsule assembly further comprises a landing zone located proximally of the abutment surface, the distal end of the capsule wall receivable in the landing zone.

In one embodiment, the landing zone has a landing zone diameter, the landing zone diameter smaller than the maximum tip portion diameter.

In one embodiment, the distal end of the capsule wall, the tip portion, the abutment surface and the landing zone are mutually shaped so as to provide a smooth transition from the lead-in surface to the distal end of the capsule wall in the second position so as to facilitate retraction of the capsule assembly through an endograft.

In one embodiment, the tail portion has a stabilizing surface that engages the inside surface of the capsule wall, the stabilizing surface having a tail end, wherein the tail end is spaced apart from the abutment surface by a distance exceeding 50% of the landing zone diameter.

According to a second aspect of the invention, there is provided a capsule assembly for an endograft introducer, the assembly comprising:
a capsule having a cavity and a capsule wall, the capsule wall having an external surface and terminating in a distal end; and
a capsule plug, the capsule plug comprising:
a tip portion having a lead-in surface and an abutment surface;
a tail portion having an external surface engageable with an inside surface of the capsule wall; and
an intermediate portion joining the tip portion to the tail portion, the intermediate portion having a landing zone, the distal end of the capsule wall receivable in the landing zone,
wherein the capsule is slidably movable with respect to the capsule plug from a first position in which the distal end of the capsule wall surrounds an opening into the cavity to a second position in which the distal end of the capsule wall is received in the landing zone providing a transition from the lead-in surface to the external surface of the capsule wall so as to facilitate retraction of the capsule assembly through an endograft.

In one embodiment, the tip portion diverges in a direction toward the intermediate portion reaching a maximum tip portion diameter.

In one embodiment, the distal end of the capsule wall has a terminal internal diameter that is resiliently expandable to allow the tip portion to move distally from the first position to the second position.

In one embodiment, the landing zone has a landing zone diameter, the landing zone diameter smaller than the maximum tip portion diameter.

In one embodiment, the distal end of the capsule wall, the tip portion, the abutment surface and the landing zone are mutually shaped so as to provide a smooth transition from the lead-in surface to the distal end of the capsule wall in the second position so as to facilitate retraction of the capsule assembly through an endograft.

In one embodiment, the tail portion has a stabilizing surface that engages the inside surface of the capsule wall, the stabilizing surface having a tail end, wherein the tail end is spaced apart from the abutment surface by a distance exceeding 50% of the landing zone diameter.

According to a third aspect of the invention, there is provided an endograft introducer comprising a nose cone dilator and a capsule assembly at a proximal end, a guide wire catheter extending distally from the nose cone dilator through the capsule assembly, a sheath and a handle, to a distal end, capsule assembly as defined by the first aspect of the invention.

According to a fourth aspect of the invention, there is provided an endograft introducer comprising a nose cone dilator and a capsule assembly at a proximal end, a guide wire catheter extending distally from the nose cone dilator through the capsule assembly, a sheath and a handle, to a distal end, capsule assembly as defined by the second aspect of the invention.

According to another aspect of the invention, there is provided a capsule for an endograft introducer, the assembly including:

a capsule having a cavity and a capsule wall, the capsule wall having an external surface and terminating in a distal end, the capsule wall having a main portion and an internally tapered portion, the internally tapered portion distal to the main portion, the internally tapered portion having a wall thickness equal to or greater than a thickness of the main portion adjacent to the internally tapered portion over all, or most of, the internally tapered portion; and a capsule plug, the capsule plug including:

a tip portion having a lead-in surface and an abutment surface; and a tail portion having an external surface engageable with an inside surface of the capsule wall, and wherein the capsule is slidably movable with respect to the capsule plug from a first position in which the distal end of the capsule wall surrounds an opening into the cavity to a second position in which the distal end of the capsule wall is positioned proximally with respect to the abutment surface, whereby movement of the tip portion into the capsule is resisted by abutment between the end of the capsule wall and the abutment surface.

BRIEF DESCRIPTION OF DRAWINGS

Embodiments of the present invention will be discussed with reference to the accompanying drawings wherein:

FIG. 2A shows a proximal end portion of a delivery device according to the invention housing a stent graft;

FIG. 2B shows a proximal end portion of a delivery device according to the invention after deployment of a stent graft and retrieval of a capsule assembly to a pusher;

FIG. 2C shows a distal end of the delivery device of FIGS. 2A and 2B;

FIGS. 10A to 10D are detailed cross-sectional views of a portion of the stent graft delivery device of FIGS. 8 and 9 in their different positions;

FIG. 13 is an isometric view of a proximal end of a delivery device according to the invention; and FIGS. 14 and 15 are isometric views of the capsule plug component of the delivery device shown in FIG. 13.

DESCRIPTION OF EMBODIMENTS

Figure 1A:
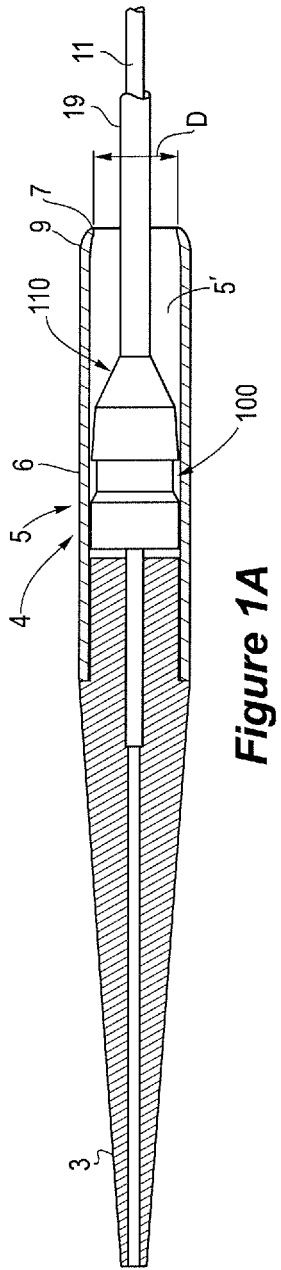
FIGS. 1A to 1C show a schematic cross-sectional view of an embodiment of the invention.

Referring to FIGS. 1A to 1C, 2A to 2C and 3, there is shown an endograft introducer, or more specifically a stent graft introducer. Very generally, the introducer 1 comprises a nose cone dilator 3 and a capsule assembly 4 at a proximal end, a guide wire catheter 11 extending distally from the nose cone dilator 3 though the capsule assembly 4, a sheath 90 and a handle 13, to a distal end, as is shown most clearly in FIG. 3. Now looking at the detailed views of the proximal end of the introducer of FIGS. 1A and 1B, the capsule assembly 4, connected to the nose cone dilator 3, is shown more clearly.

Again turning to FIGS. 1A and 1B, the capsule assembly 4 may be made from radiopaque nylon and comprises a capsule 5 defining a cavity 5'. The struts of an exposed stent 37 at the proximal end 36 of a stent graft 35 are received in the cavity 5', as is shown in FIG. 2A. The capsule 5 also includes a capsule wall 6 terminating in a distal end 7.

The capsule assembly 4 also includes a capsule plug 100 comprising a tip portion 110, an intermediate portion 120 and a tail portion 130. The tip portion 110 has a lead-in surface 111, 112 and an abutment surface 118. The tail portion has an external stabilizing surface 132 that is engageable with an inside surface 8 of the capsule wall 6. The intermediate portion 120 joins the tip portion 110 to the tail portion 130. The intermediate portion 120 has a landing zone 122 and the distal end 7 of the capsule wall 6 is receivable in the landing zone 122, as is shown in FIG. 1B.

Figure 1B:
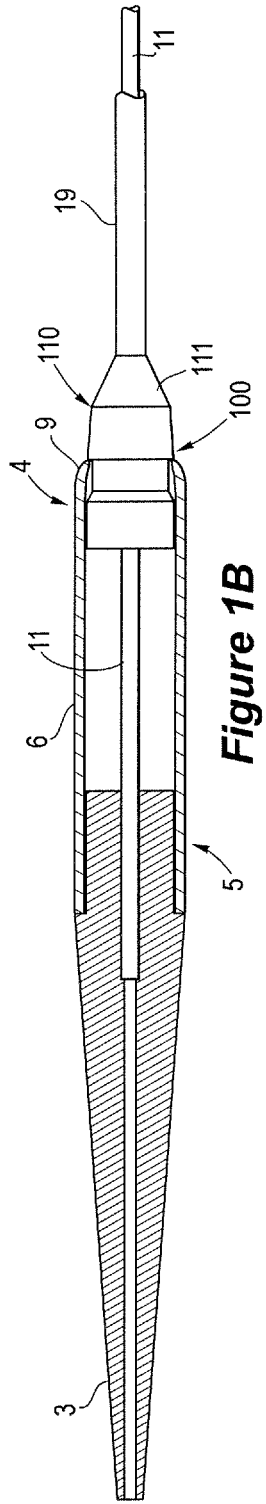
Figure 3:
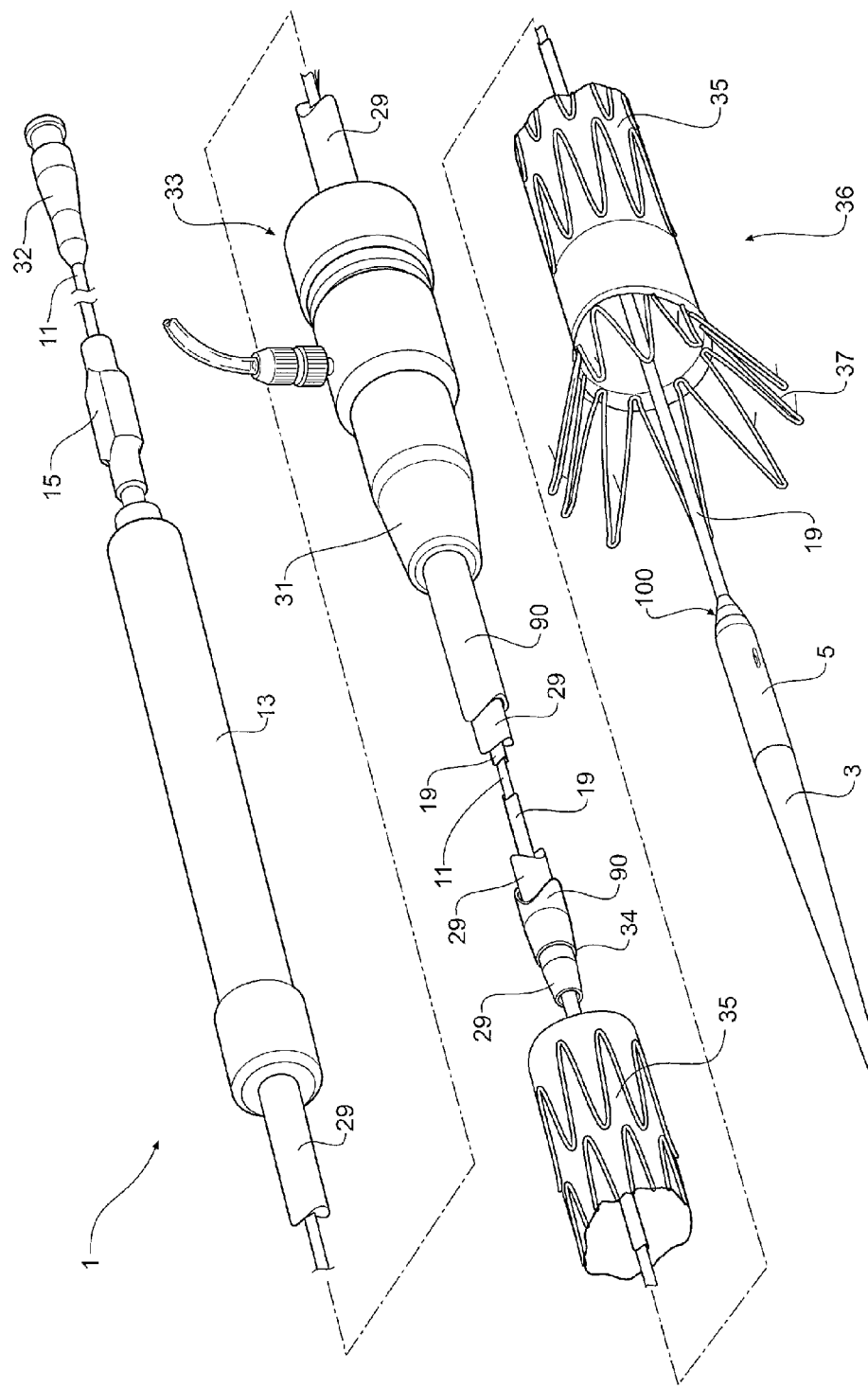
FIG. 3 is an isometric view of a stent graft delivery device according to the invention with the capsule plug in a position to facilitate withdrawal of the proximal end of the delivery device.

Referring to FIGS. 1A and 1B, it can be seen that the capsule wall 6 is slidably moveable with respect to the capsule plug 100 from a first position, shown in FIG. 1A, in which the distal end 7 of the capsule wall 6 surrounds an opening into the capsule cavity 5' to a second position in which the distal end 7 of the capsule wall 6 is received in the landing zone 122, as shown in FIG. 1B. A transition 112 from the lead-in surface 111 to the distal end 7 of the capsule wall 6 is provided so as to facilitate retraction of the capsule assembly 4 through a stent graft 35, as is shown in FIG. 3.

Figure 1C:
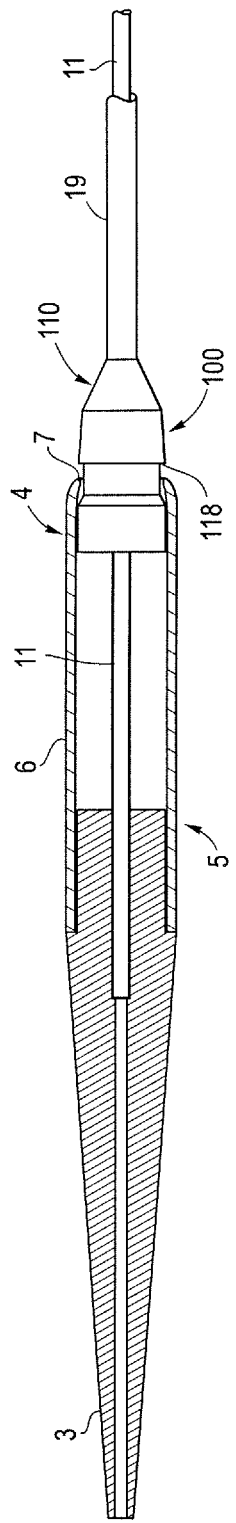

Referring to FIGS. 1A to 1C, it can be seen that the capsule wall 6 has a slightly radially in-turned distal end 7. This has two purposes. The first is to assist with engagement of a sheath 90, particularly during assembly of the stent graft introducer, when the sheath 90 is advanced over the distal end 7 of the capsule wall 6, as shown in FIG. 2A. The second is to prevent complete withdrawal of the capsule plug 100 from the capsule 5, as is illustrated in FIG. 1C. This will be described in more detail with reference to FIGS. 4A, 4B, 4C and FIGS. 5 to 6 and then 7 to 9.

Referring again to FIG. 1A, the distal end 7 of the capsule wall 6 has a terminal internal diameter D that is resiliently expandable to allow the tip portion 110 of the capsule plug 100 to move distally from the first position shown in FIG. 1A to the second position shown in FIG. 1B.

Referring to FIGS. 2A to 2C and 3, it can be seen that a pin vice arrangement 15 at the distal end 14 of the handle 13 locks movement of the guide wire catheter 11 with respect to the handle 13. The pin vice arrangement can be loosened to allow relative movement between the guide wire catheter 11 and the handle 13.

FIG. 2A shows the capsule 5 and the capsule plug 100 partially surrounded by the sheath 90 in a ready to deploy condition. The capsule plug is at the proximal end of the recess 5' and the struts of the exposed stent 27 at the proximal end 36 of a stent graft 35, are received into the capsule cavity 5'.

Again referring to FIG. 3, it can be seen that from the handle 13 extends a pusher catheter 29 through a sheath manipulator 31 to which is connected the sheath 90. In FIG. 3, the stent graft 35 has been released and all of the trigger wire release devices, which are depicted on the handle in FIG. 2C, have been removed. The guide wire catheter 11 extends from a Luer lock connector 32 at the distal end of the device through the pin vice 15, handle 13, and pusher catheter 29 to the nose cone dilator 3 at the proximal end of the delivery device 1.

The nose cone dilator 3 and the capsule 5 will generally be fabricated as separate components and then glued together, however they may be fabricated in a single assembly.

Referring to FIGS. 4A to 4C, 5 and 6, the capsule plug 100 and its relationship to the distal end 7 of the capsule wall 6 is shown. It can be seen from these drawings that the distal end 7 of the capsule wall 6 tapers internally with an internally tapered portion 7a before tapering externally with an externally tapered portion 7b, resulting in a slight thickening before thinning to an end 7c, as is illustrated most clearly in FIG. 4b. This thickening provides the capsule recess 5' with an exit that strongly resists expansion and hence resists movement over the short taper section 138. The relatively steep taper on the taper section 138 further assists in resisting this movement.

Figure 4A:
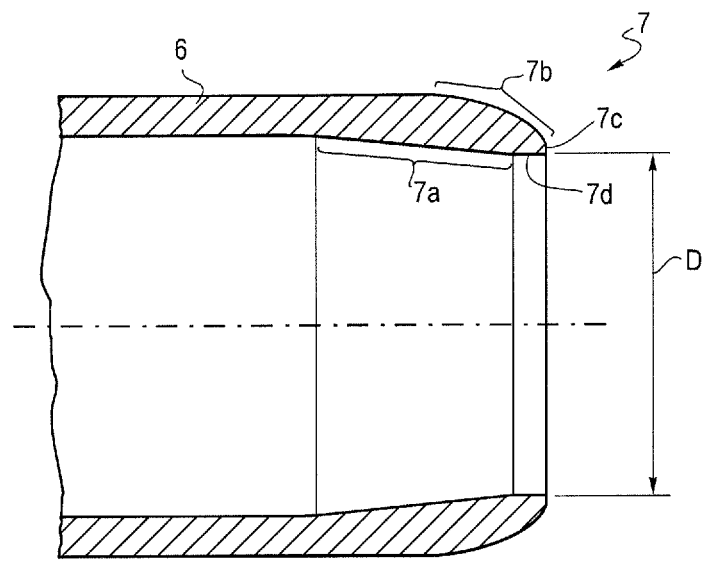
FIGS. 4A, 4B, and 4C show a detailed view of a portion of the capsule assembly of the embodiment shown in FIGS. 1A to 1C.
Figure 4B:
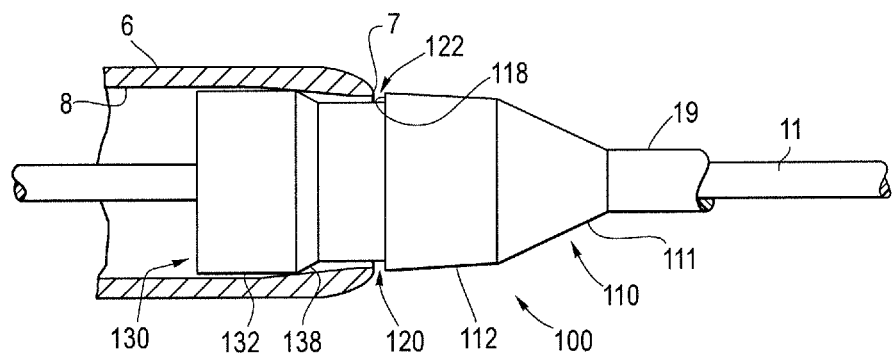
Figure 4C:
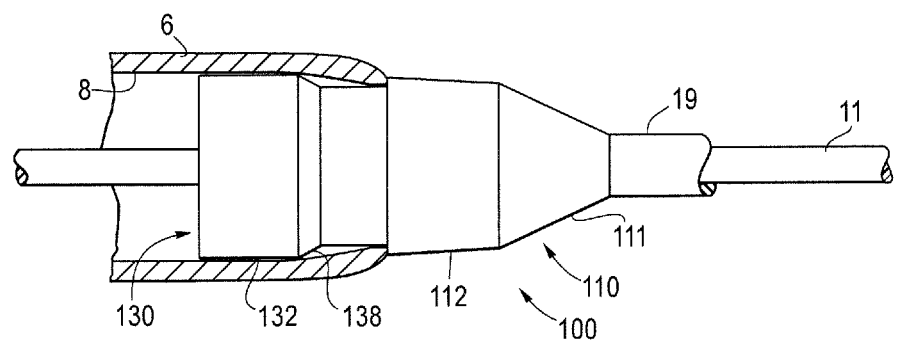

Referring to FIGS. 1B and 4C, it can be seen that the distal end 7 of the capsule wall 6, the tip portion 110, the abutment surface 118 and the landing zone 122 of the capsule plug are mutually shaped so as to provide a smooth transition from the lead-in surface to the distal end 7 of the capsule wall 6 in the second position, so as to facilitate smooth retraction of the capsule assembly 4 through an endograft or stent graft 35.

The distal end 7 terminates with an end 7c that is substantially flat for abutment with the abutment surface 118 of the capsule plug 100.

The interaction between the abutment surface 118 and the end 7c provides a compressive resistance. Any relative movement between the capsule 5 and the capsule plug 100, once in the position shown in FIG. 1B, will be strongly resisted in compression.

The internal bore of the capsule has parallel sided terminal portion 7d, as is shown in FIG. 4A. The thickness of the end 7c measured in a radial direction added to the landing zone diameter d2 is approximately equal to the maximum tip portion diameter $d_1$. This results in the smooth transition from the capsule plug 100 lead-in surface 111 to the outside surface 9 of the capsule wall 6, as is shown in FIGS. 1B and 4C, so as to facilitate retraction of the capsule assembly through a stent graft 35. It can also facilitate retraction through a potentially winding and pulsating aorta, past the proximal end 34 of the sheath 90, through the sheath 90 and then through the Captor™ valve 33.

Referring again to FIG. 4C, the capsule plug 100 is shown in more detail. From this figure, it can be seen that a stabilizing surface 132 on the tail portion 130 engages the inside surface 8 of the capsule wall 6. This stabilizing surface 132 has sufficient length so as to provide stability to the capsule assembly 4 in bending (the stabilizing surface 132 has a tail end, the tail end spaced apart from the abutment surface 118 by a distance exceeding 50% of the landing zone diameter). This is important because the delivery system must track through sometimes quite torturous vasculature from an incision in the femoral artery. Specifically, the stabilizing surface 132 has been found to be effective in preventing the capsule plug 100 from dislodging from its retrieval position, as is illustrated in FIG. 1B. It is also effective in ensuring that there remains a smooth transition from the lead-in surface 111 of the capsule plug tip portion 110 to the distal end 7 of the capsule wall 6.

Also apparent from FIGS. 4B and 4C is a short taper section 138. This short taper section 138 provides resistance to the shallow internal taper of the capsule wall 6 at internal tapered portion 7a, so as to provide adequate resistance in the tension position illustrated in FIGS. 1C and 4B. This is particularly important in preventing the capsule plug 100 from being fully removed from the capsule 5.

Figure 5:
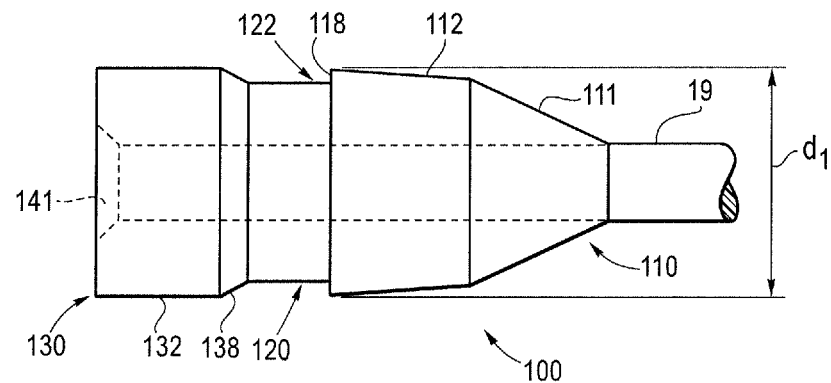
FIGS. 5 and 6 show side views and isometric views respectively of a capsule plug component of the embodiment of the invention shown in FIGS. 1A to 1C.
Figure 6:
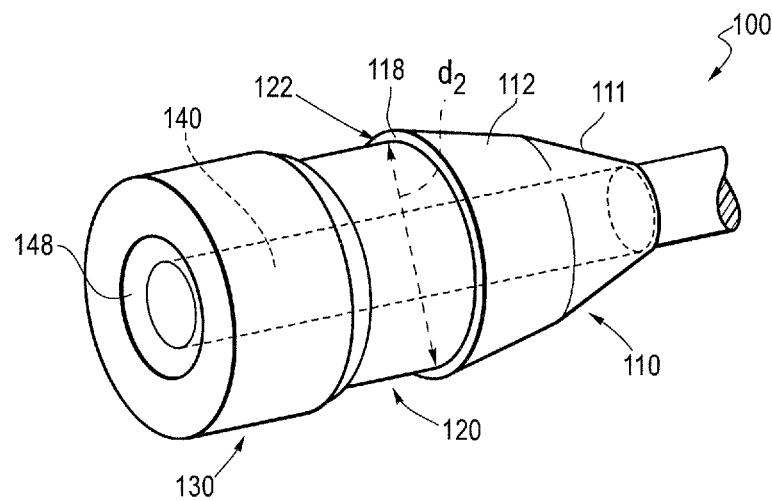

FIGS. 5 and 6 also show that the tip portion 110 diverges in a direction towards the intermediate portion 120, reaching a maximum tip portion diameter just before an abutment surface 118. This provides a lead-in surface 111.

The capsule plug 100 may be made from various biocompatible materials including stainless steel. It fits coaxially around the guide wire catheter 11 enabling the guide wire catheter 11 to move longitudinally within the capsule plug 100. A plug sleeve 19 is mounted coaxially around the guide wire catheter 11 and the guide wire catheter 11 can move longitudinally within the plug sleeve 19. At its proximal end, the plug sleeve 19 is joined to the capsule plug tip portion 110, as is shown in FIGS. 1A to 1C. The plug sleeve 19 may be made from a polymer such as polyether ether ketone (PEEK) and may be bonded to the capsule plug 100 by a suitable adhesive. For instance, the plug sleeve 19 may be bonded to the capsule plug 100 at an attachment surface 148, as is shown in FIG. 6.

At its distal end, the plug sleeve 19 terminates at the handle 13, as is diagrammatically illustrated in FIG. 2C.

Figure 7:
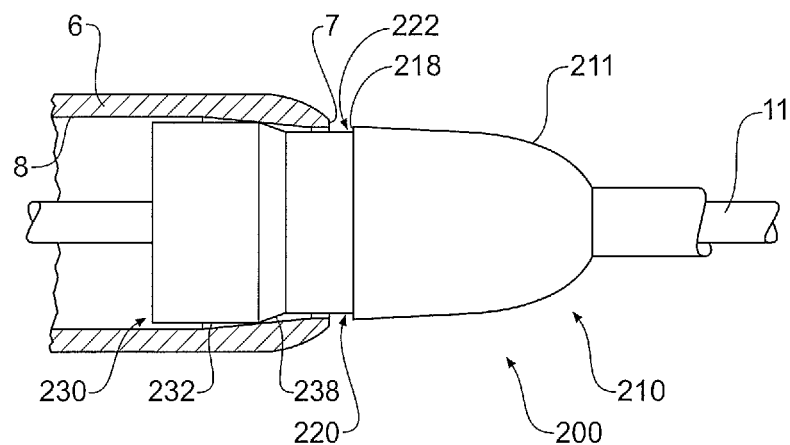
FIG. 7 is a similar view to that of FIG. 4B, but shows a portion of an alternative embodiment of the invention.
Figure 8:
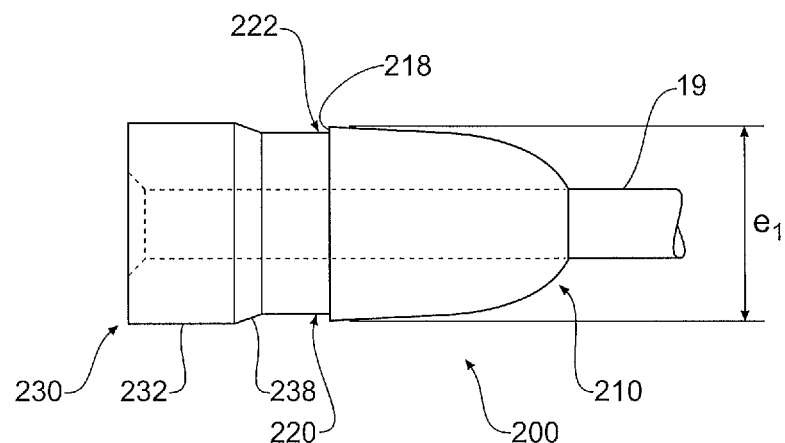
FIGS. 8 and 9 are similar views to those of FIGS. 5 and 6 but show a capsule plug component of the alternative embodiment shown in FIG. 7.
Figure 9:
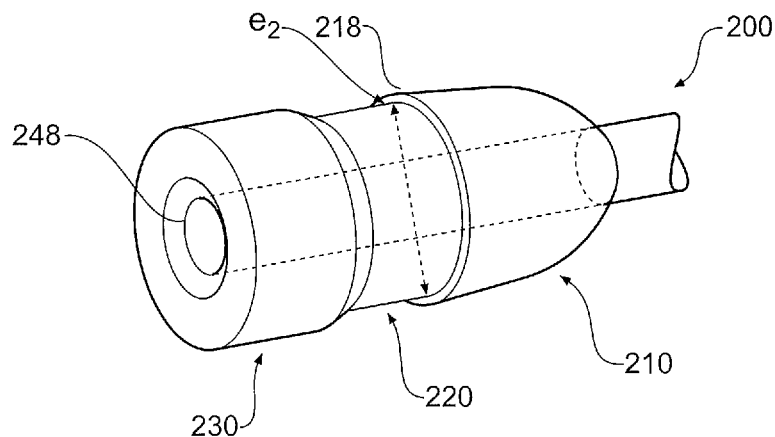

An alternative capsule plug 200 is shown in FIGS. 7, 8 and 9. With the capsule plug 200, the tip portion 210 has a divergence that decreases in a direction toward the intermediate portion 220 to provide a bullet shape.

The capsule plug 200 is in other respects similar to the capsule plug 100 described above and shown in FIGS. 5 and 6 (having a tip portion 210, an intermediate portion 220 and a tail portion 230). The tip portion 210 has a lead-in surface 211 and an abutment surface 218. The tail portion has an external stabilizing surface 232 that is engageable with an inside surface 8 of the capsule wall 6. The intermediate portion 220 joins the tip portion 210 to the tail portion 230. The intermediate portion 220 has a landing zone 222 and the distal end 7 of the capsule wall 6 is receivable in the landing zone 222.

In order to better understand how the capsule assembly 4 can be used, the interface between a stent graft 35 and the introducer 1 is shown in more detail in FIGS. 10A, 10B, 10C and 10D. These figures show in detailed cross-section a portion of a stent graft delivery device 1 according to an embodiment of the present invention. FIG. 10A is similar to that of FIG. 1A but shows additional detail, including the stent graft 35 and its exposed stent 37. In FIG. 10A, the exposed stent 37 is received into the capsule cavity 5' and is prevented from being prematurely removed from the capsule 5 by the use of a trigger wire 39, which passes through the stent graft 35 to the outside of the capsule 5 and then enters the capsule 5 through aperture 41 in the capsule wall 6. The trigger wire 39 then passes through one of the bends 43 of the exposed stent 37 and then past the tapered plug device 17 and into an aperture 47 in the nose cone dilator 3.

To enable the trigger wire 39 to pass the tapered capsule plug 100, there is a longitudinal slot 45 in the plug 100. It will be noted that at this stage, the plug 100 does not interfere with the retention of the exposed stent into the capsule.

In FIG. 10B, the trigger wire 39 has been removed and the nose cone dilator 3 and capsule 5 have been advanced proximally by movement of the guide wire catheter 11, as indicated by the arrow 49 with respect to the handle 13. The exposed stent 37 is still partly retained in the capsule. The tapered plug device 17 has in effect moved towards the distal end 7 of the capsule 5.

In FIG. 10C, the nose cone dilator 3 and capsule 5 have been advanced further proximally by movement of the guide wire catheter 11 with respect to the handle 13 until the exposed stent 37 has been released from the capsule 5. At this stage, the capsule plug 100 is still not fully extended from the capsule or locked in place.

In FIG. 10D, the capsule plug 100 is shown fully extended from the capsule 5 and is locked in place by the interaction between the abutment surface 118 and the end 7c. This interaction provides a compressive resistance. Any relative movement between the capsule 5 and the capsule plug 100, once in the position shown in FIG. 1B, will be strongly resisted in compression.

Figure 11:
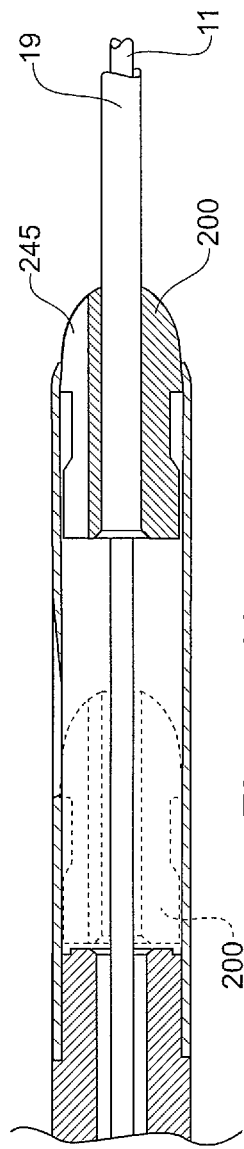
FIG. 11 is a detailed cross-sectional view of a portion of a stent graft delivery device according to the alternative embodiment of the invention shown in FIGS. 7, 8 and 9.

Referring now to FIG. 11, a detailed cross-section of a portion of a stent graft delivery device 1 according to an alternative embodiment of the present invention is shown. In this embodiment, the plug 200 has a surface shape of a distally facing bullet. The plug 200 has a slot 55 to allow a trigger wire 39 to pass the plug 200. The dotted lines indicate the position of the capsule plug 200 during introduction of the stent graft 35.

Figure 12:
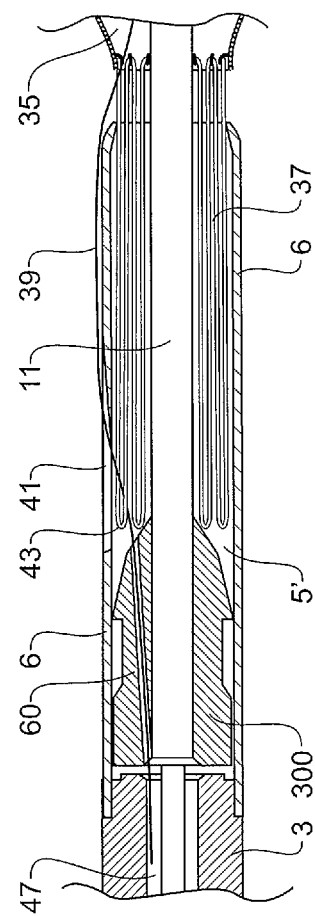
FIG. 12 is a detailed cross-sectional view of a portion of a stent graft delivery device according to yet another embodiment of the invention.

FIG. 12 is similar to that of FIG. 10A but shows an alternative capsule plug 100 being used with the stent graft 35 and its exposed stent 37. This capsule plug 100 is shown in FIGS. 15 and 16 and has at least one aperture 60 (as opposed to the slot 55 of the capsule plug 200 of FIG. 11) for enabling the trigger wire 39 to pass the tapered capsule plug 100.

In FIG. 12, again the exposed stent 37 is received into the capsule cavity 5' and is prevented from being prematurely removed from the capsule 5 by the use of a trigger wire 39, which passes through the stent graft 35 to the outside of the capsule 5 and then enters the capsule 5 through aperture 41 in the capsule wall 6. The trigger wire 39 then passes through one of the bends 43 of the exposed stent 37 and then past the tapered plug device 17 and into an aperture 47 in the nose cone dilator 3. In this respect, it is the same as the arrangement shown in FIG. 10A. However, to enable the trigger wire 39 to pass the tapered capsule plug 100, there is an aperture 60 (instead of a longitudinal slot 45) in the plug 100.

FIG. 13 is an isometric view of a proximal end of the delivery device 1. This drawing shows the capsule plug 100 and capsule 5 prior to assembly.

FIGS. 14 and 15 are isometric views of the capsule plug component of the delivery device shown in FIG. 13.

The operation of the embodiment of the invention illustrated in FIG. 3 will now be described.

The environment in which the capsule assembly 4 is typically used is within the aorta of a patient, proximal to an aortic aneurism. Blood pulses past the delivery device 1 and hence the capsule assembly 4 as it tracks through what is often a torturous vasculature from an incision in the femoral artery.

The delivery system 1 is positioned such that the stent graft 35 is aligned in the area of treatment, which places the nose cone dilator 3 and the capsule assembly 4 proximal to the aneurism. At this point, various stent graft deployment steps are taken as is known in the art and it is only when the proximal stent 37 is ready for deployment that the capsule plug 100 of the capsule assembly 4 is activated, as will now be described.

The proximal exposed stent 37 is deployed by removing the trigger wire 39 end by pulling the trigger wire 39 out of the slot 45 (or aperture 60). The pin vice arrangement 15 is then released. The guide wire catheter 11 is then pushed at its distal end in a proximal direction. This movement in the direction of arrow 49, as shown in FIG. 10B, slides the capsule 5 off the exposed stent 37 and is stopped when the capsule plug 100 snaps into locking engagement with the distal end 7 of the capsule wall 8 into the position shown in FIG. 1B.

The locking mechanism in the form of pin vice 15 (as is shown in FIG. 3) is reactivated to lock the sleeve 19 and the guide wire catheter 11 together and then the nose cone dilator 3 and capsule assembly 4 are retrieved as the distal attachment of the stent graft 35 is removed, docking the capsule plug 100 with the proximal end of the pusher catheter 29 (these components are most clearly shown in FIG. 3). This docked position is shown in FIG. 2B.

In some applications, the capsule 4 will form part of a more complex introducer than the introducer 1 illustrated in FIG. 3. For instance, an introducer with a two-part handle such as that shown and described in the applicant's earlier patent publication number US2010/0198328 (Hartley et al.), titled *Preloaded Stent Graft Delivery Device*, can be used for deployment of fenestrated stent grafts that have fenestrations for branch vessels (the contents of this publication is hereby incorporated by reference in its entirety). Such a handle may resemble the handle shown in FIG. 2C with locking screws 56, 57, 58 and 59 provided for release and trigger wires. With such more complex introducers and their stent grafts, it is not until after cannulation of the fenestrations is complete and associated accessories removed that the pusher catheter 29 is retrieved through the sheath 90, leaving the nose cone dilator 3 and capsule assembly 4 in place until the handle pieces 13 come together. Finally, the nose cone dilator 3 and capsule assembly 4 are removed via the sheath 90 by pulling them through the Captor™ valve 33.

It has been found that the capsule assembly 4 offers a number of advantages over earlier capsule assembly arrangements. For instance, the capsule plug 100 is far more stable and will not readily dislodge even as the delivery device 1 is manipulated through torturous vasculature systems. Furthermore, the capsule assembly 4 does not rely on tension in the PEEK plug sleeve 19 to hold the capsule 100 in its retrieval position, as is shown in FIG. 1B.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The disclosures in Australian patent application number 2013257415, European Patent serial number 14275159.3, from which this application claims priority, and in the abstract accompanying this application are incorporated herein by reference.

What is claimed is:

1. A capsule assembly for an endograft introducer, the assembly comprising:
a capsule having a cavity and a capsule wall, the capsule wall having an external surface and terminating in a distal end; and
a capsule plug, the capsule plug comprising:
a tip portion having a lead-in surface and an abutment surface; and
a tail portion having an external surface engageable with an inside surface of the capsule wall, and
a landing zone located proximally of the abutment surface, the distal end of the capsule wall receivable in the landing zone, the landing zone having a landing zone diameter,
wherein the capsule is slidably movable with respect to the capsule plug from a first position in which the distal end of the capsule wall surrounds an opening into the cavity to a second position in which the distal end of the capsule wall is positioned proximally with respect to the abutment surface, whereby movement of the tip portion into the capsule is resisted by abutment between the distal end of the capsule wall and the abutment surface,
wherein the tip portion diverges in a direction toward the tail portion reaching a maximum tip portion diameter at a location adjacent to or distal of the abutment surface,
wherein the distal end of the capsule wall has a terminal internal diameter that is resiliently expandable to allow the tip portion to move distally from the first position to the second position, and
wherein the tail portion has a stabilizing surface that engages the inside surface of the capsule wall, the stabilizing surface having a tail end, wherein the tail end is spaced apart from the abutment surface by a distance exceeding 50% of the landing zone diameter.

2. The capsule assembly as claimed in claim 1, wherein the tip portion comprises a first divergent portion and a second divergent portion, the first divergent portion diverging towards the second divergent portion and the first divergent portion diverging more steeply than the second divergent portion.

3. The capsule assembly as claimed in claim 1, wherein the tip portion divergence decreases in a direction toward the intermediate portion.

4. The capsule assembly as claimed in claim 1, wherein the landing zone has a landing zone diameter, the landing zone diameter smaller than the maximum tip portion diameter.

5. The capsule assembly as claimed in claim 4, wherein the distal end of the capsule wall, the tip portion, the abutment surface and the landing zone are mutually shaped so as to provide a smooth transition from the lead-in surface to the distal end of the capsule wall in the second position so as to facilitate retraction of the capsule assembly through an endograft.

6. An endograft introducer comprising a nose cone dilator and a capsule assembly at a proximal end, a guide wire catheter extending distally from the nose cone dilator through the capsule assembly, a sheath and a handle, to a distal end, the capsule assembly as defined by claim 1.

7. A capsule assembly for an endograft introducer, the assembly comprising:
a capsule having a cavity and a capsule wall, the capsule wall having an external surface and terminating in a distal end; and
a capsule plug, the capsule plug comprising:
a tip portion having a lead-in surface and an abutment surface;
a tail portion having an external surface engageable with an inside surface of the capsule wall; and
an intermediate portion joining the tip portion to the tail portion, the intermediate portion having a landing zone, the landing zone having a landing zone diameter, the distal end of the capsule wall receivable in the landing zone,
wherein the capsule is slidably movable with respect to the capsule plug from a first position in which the distal end of the capsule wall surrounds an opening into the cavity to a second position in which the distal end of the capsule wall is received in the landing zone providing a transition from the lead-in surface to the external surface of the capsule wall so as to facilitate retraction of the capsule assembly through an endograft, and
wherein the tail portion has a stabilizing surface that engages the inside surface of the capsule wall, the stabilizing surface having a tail end, wherein the tail end is spaced apart from the abutment surface by a distance exceeding 50% of the landing zone diameter.

8. The capsule assembly as claimed in claim 7, wherein the tip portion diverges in a direction toward the intermediate portion reaching a maximum tip portion diameter.

9. The capsule assembly as claimed in claim 8, wherein the terminal internal diameter that is resiliently expandable to allow the tip portion to move distally from the first position to the second position.

10. The capsule assembly as claimed in claim 9, wherein the landing zone diameter smaller than the maximum tip portion diameter.

11. The capsule assembly as claimed in claim 10, wherein the distal end of the capsule wall, the tip portion, the abutment surface and the landing zone are mutually shaped so as to provide a smooth transition from the lead-in surface to the distal end of the capsule wall in the second position so as to facilitate retraction of the capsule assembly through an endograft.

12. An endograft introducer comprising a nose cone dilator and a capsule assembly at a proximal end, a guide wire catheter extending distally from the nose cone dilator through the capsule assembly, a sheath and a handle, to a distal end, the capsule assembly as defined by claim 7.

13. A capsule assembly for an endograft introducer, the assembly including:
    a capsule having a cavity and a capsule wall, the capsule wall having an external surface and terminating in a distal end, the capsule wall having a main portion and an internally tapered portion, the internally tapered portion distal to the main portion, the internally tapered portion having a wall thickness greater than a thickness of the main portion adjacent to the internally tapered portion; and
    a capsule plug, the capsule plug including:
        a tip portion having a lead-in surface and an abutment surface;
        a tail portion having an external surface engageable with an inside surface of the capsule wall; and
        a landing zone between the tip portion and the tail portion for receiving the distal end of the capsule wall; wherein the landing zone has a landing zone diameter;
    wherein the capsule is slidably movable with respect to the capsule plug from a first position in which the distal end of the capsule wall surrounds an opening into the cavity to a second position in which the distal end of the capsule wall is positioned proximally with respect to the abutment surface, whereby movement of the tip portion into the capsule is resisted by abutment between the end of the capsule wall and the abutment surface, and
    wherein the tail portion has a stabilizing surface that engages the inside surface of the capsule wall, the stabilizing surface having a tail end, wherein the tail end is spaced apart from the abutment surface by a distance exceeding 50% of the landing zone diameter.

\* \* \* \* \*